(12) United States Patent  
van den Nieuwenhof et al.

(10) Patent No.: US 7,197,361 B2  
(45) Date of Patent: Mar. 27, 2007

(54) CARDIAC LEAD WITH ANODIC ELECTRODE ASSEMBLY HAVING DUAL SUPPORT HULLS

(75) Inventors: Ronald A. van den Nieuwenhof, Odessa, FL (US); Mohammed N. Islam, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 188 days.

(21) Appl. No.: 10/911,975

(22) Filed: Aug. 5, 2004

(65) Prior Publication Data

US 2005/0060013 A1 Mar. 17, 2005

Related U.S. Application Data

(60) Provisional application No. 60/493,847, filed on Aug. 8, 2003.

(51) Int. Cl.  
*A61N 1/05* (2006.01)

(52) U.S. Cl. .................. 607/116; 600/372

(58) Field of Classification Search .......... 607/116; 600/372–382  
See application file for complete search history.

(56) References Cited

U.S. PATENT DOCUMENTS

| 4,381,014 A | 4/1983 | Sandstrom et al. |
| 4,590,950 A | 5/1986 | Iwaszkiewicz |
| 4,628,943 A | 12/1986 | Miller |
| 5,251,643 A * | 10/1993 | Osypka ............ 607/122 |
| 6,501,991 B1 * | 12/2002 | Honeck et al. ...... 607/122 |

FOREIGN PATENT DOCUMENTS

| DE | 3043 189 A1 | 6/1982 |
| DE | 37 18324 A1 | 12/1988 |
| FR | 2 491 763 | 10/1981 |

* cited by examiner

*Primary Examiner*—Robert E. Pezzuto  
*Assistant Examiner*—Eric D. Bertram  
(74) *Attorney, Agent, or Firm*—Scott D. Wofsy; Edwards Angell Palmer & Dodge LLP

(57) ABSTRACT

An electrode assembly for an elongated implantable lead containing conducting filars. The electrode assembly has a first support hull surrounding a portion of the lead. The electrode assembly also has an electrode hull for at least partially surrounding the support hull and a portion of the lead adjacent to the support hull. The electrode hull secures to the support hull and to the lead at a location axially spaced from the support hull, such that the electrode hull, the support hull, and the lead define a gap. The gap allows the conducting filars to operatively connect to the first support hull.

18 Claims, 3 Drawing Sheets

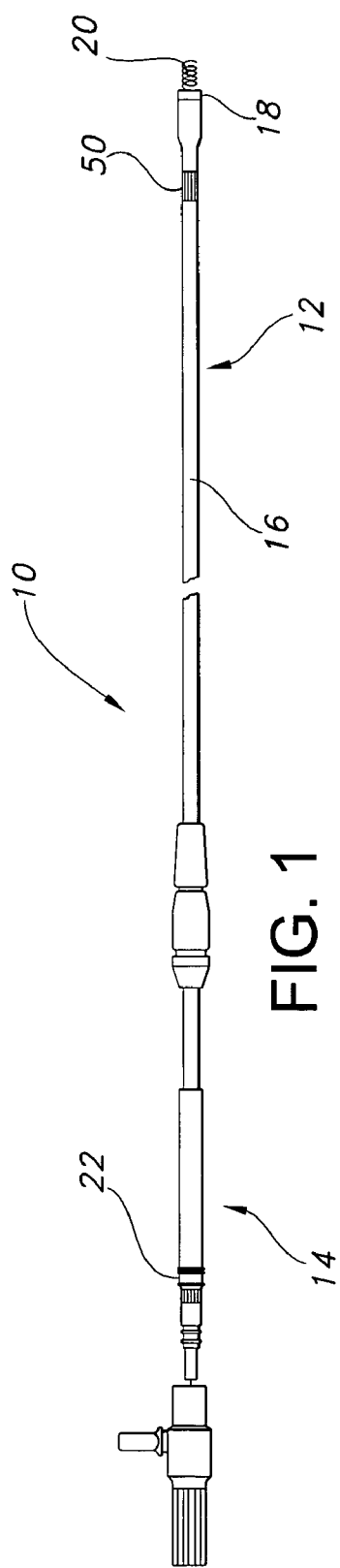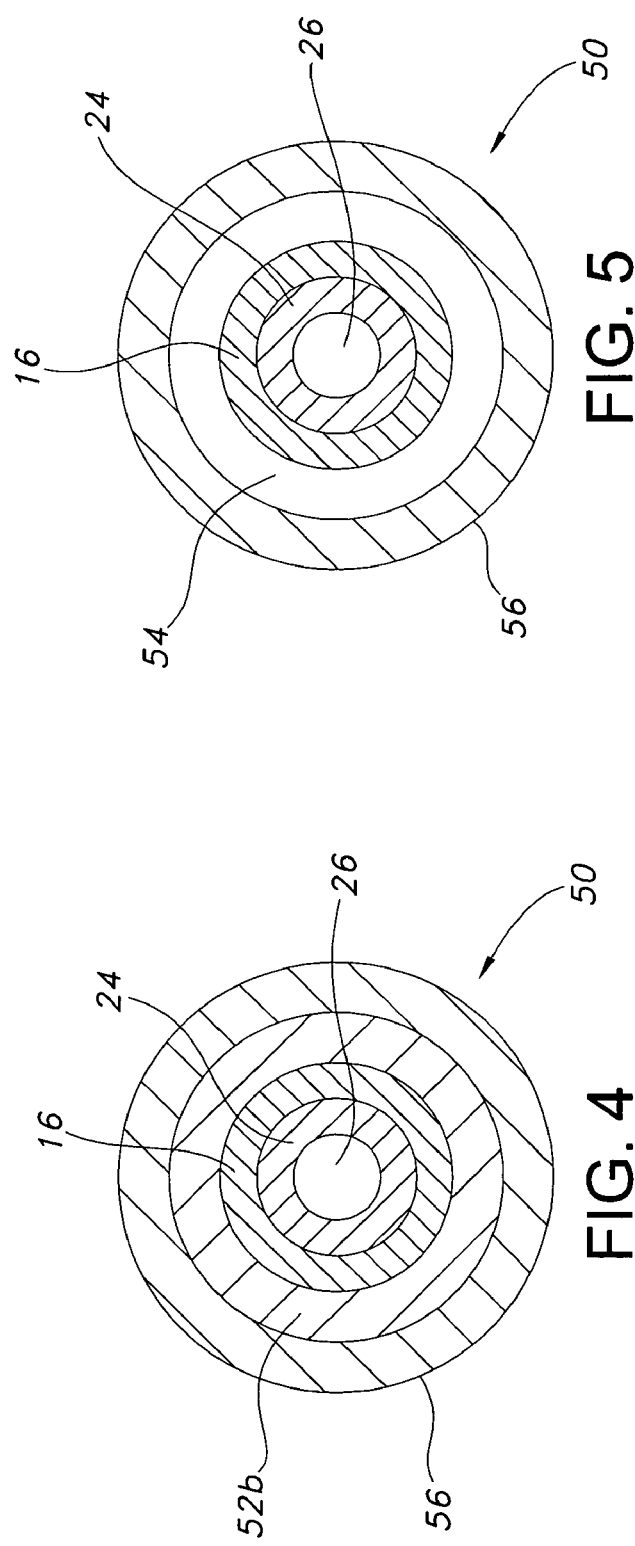

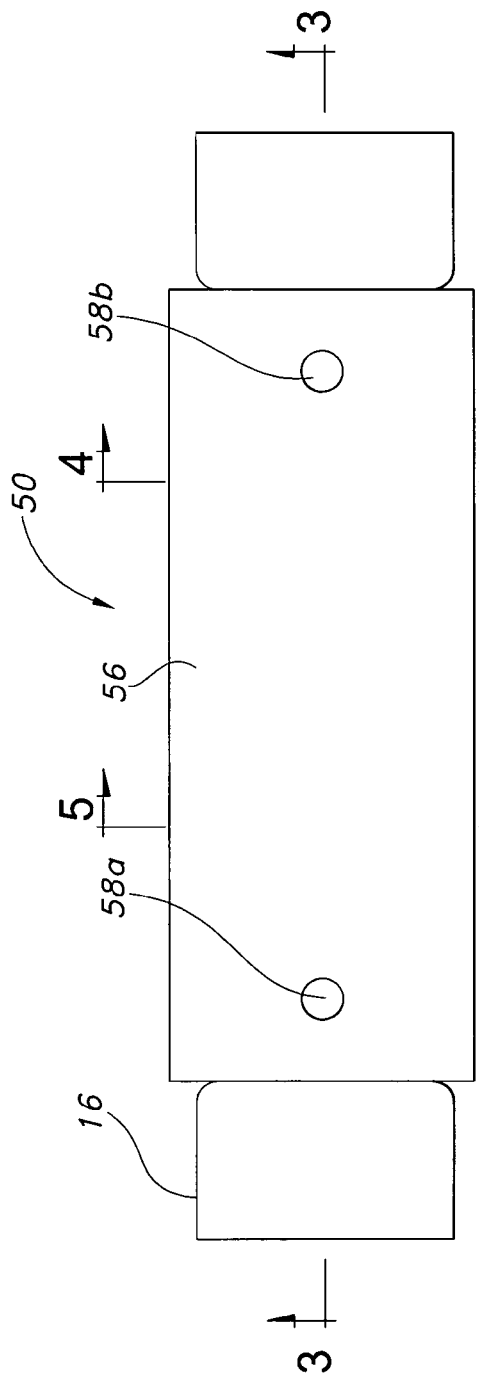
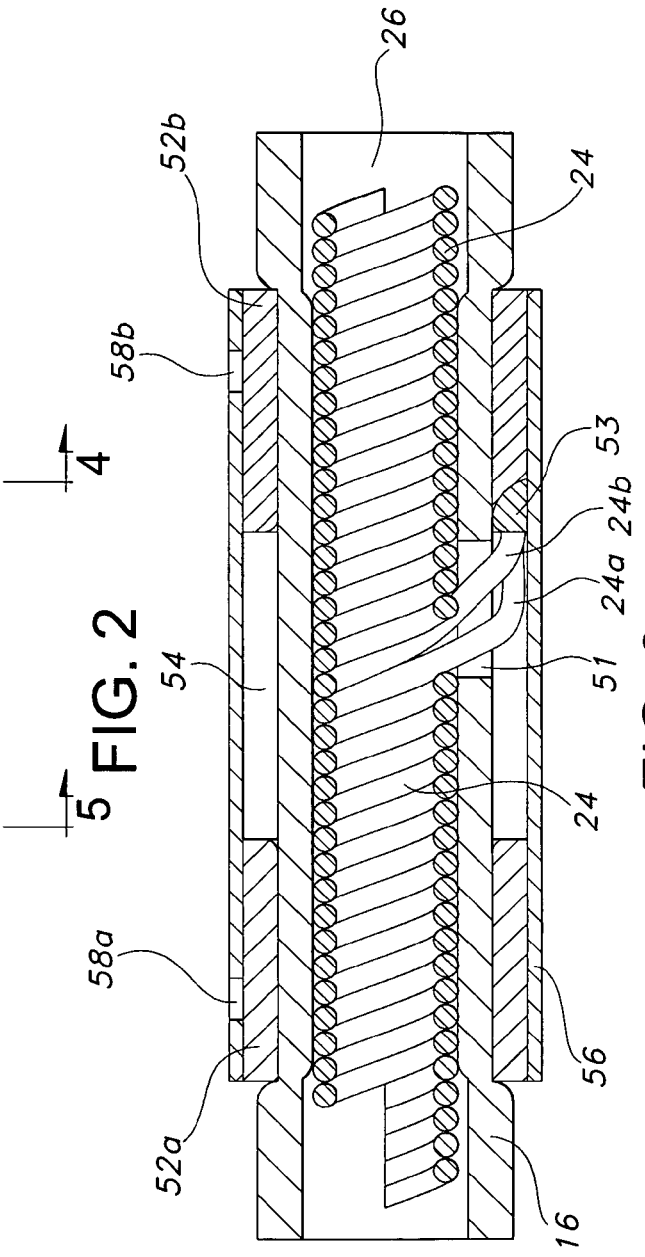

CARDIAC LEAD WITH ANODIC ELECTRODE ASSEMBLY HAVING DUAL SUPPORT HULLS

CROSS-REFERENCE TO RELATED APPLICATION

The subject application claims the benefit of commonly-owned, co-pending U.S. Provisional Patent Application Ser. No. 60/493,847, filed Aug. 8, 2003, the disclosure of which is herein incorporated by reference.

BACKGROUND OF THE INVENTION

1. Field of the Invention

The subject disclosure relates to implantable medical leads in general, and more particularly to an implantable bipolar cardiac lead with an anodic electrode assembly having dual support hulls.

2. Background of the Related Art

Abnormal heart beats, knows as arrhythmias, can include a heart beating too rapidly, too slowly, or irregularly. These conditions can be treated by applying electrical energy to the heart. It is, however, important that this treatment be implemented shortly after the onset of an episode of arrhythmia, as episodes not treated within minutes can be fatal.

One method for applying electrical energy to the heart is to implant a pulse generating device in the body that senses arrhythmia and administers an appropriate amount of electrical energy to the heart tissue. The pulse generator is connected to the heart using one or more cardiac leads, each incorporating one or more electrodes that directly engage the heart. Because these leads and electrodes are a necessary part of a life-sustaining process, it is essential that they operate reliably for long periods of time. Further, because these devices are implanted as part of an invasive procedure, and then remain permanently inside the body, it is preferred that they be as small as possible.

There are two major types of cardiac leads in use. Unipolar leads are those that provide only one electrode (the cathode) for electrical connection to the heart. Electrical impulses travel through the lead and electrode to the heart and then return through the person's body to the generating device (which serves as the anode) to complete the circuit. Bipolar leads provide two electrodes for connecting to the heart, a cathode and an anode. Electrical impulses travel through the cathode, continue a short distance through the heart, and then reach the anode which completes the circuit. Bipolar leads are generally preferred over unipolar due to their greater insensitivity to extraneous electromagnetic interference. However, bipolar leads typically have the disadvantage of being larger than unipolar leads.

Several alternative configurations for bipolar cardiac leads have been developed previously. For example, see U.S. Pat. No. 4,590,950 of Iwaszkiewicz; U.S. Pat. No. 4,628,943 of Miller; French patent application No. 81 19037 of Sandstrom et al.; and German patent application No. 37 18 324 A1 of Hirschberg. Despite such advances in the field, many teachings lack a positive electrical connection between the anodic electrodes contacting the heart and the conductors within the leads that supply electrical impulses from the generating device. This lack of positive connection leads to reduced mechanical reliability of the lead.

One invention which does not suffer from the above drawback is presented in German patent application No. 30 43 189 C3 to Osypka ("the '189 application"). The '189 application discloses an electrode 1 in which several conductors 5,6 arranged in a multiple helix extending through a hose 7. Some of the conductors connect to a pole 4 at the end of the electrode 1, while others pass through the hose 7 and are affixed to a pole 3 located around the hose 7. This configuration provides a positive electrical connection between the conductors 5,6 and the poles 3,4. Further, the connections remain completely shielded from the body's environment by the pole 3 and hose 7. However, the solid structure of the pole 3 disclosed in the '189 application makes the process of attaching the conductor 5 quite difficult.

U.S. Pat. No. 5,251,643 to Osypka ("the '643 patent") discloses a cardiac pacemaker lead 1 having a proximal end 1a and a distal end 1b, the distal end 1b having a first pacing electrode 15. A first helically wound, wire-like conductor 4 is connected to the first pacing electrode 15 and extends toward the proximal end 1a. A second helically wound wire-like conductor 3 similarly extends toward the proximal end 1a. A first tubular, sheath-like insulator 9 surrounds the convolutions of the conductor 3 and extends all the way to the electrode 15. A second tubular, sheath-like insulator 8 is disposed between the conductors 3,4 and also extends all the way to the electrode 15. A tubular fourth conductor 7 is confined between the convolutions of the conductor 3 and the insulator 8 and its distal end 7a is electrically connected to the conductor 3 at its last convolution 3d using a solder or weld joint 3c. A sleeve-like second pacing electrode 5 is fit on an adjacent portion of the insulator 9 at a location 2 between the electrode 15 and the proximal end 1a. An elongated, band-shaped third conductor 6 has a second portion 6a attached to the conductor 7 by solder or weld joints 13a. An intermediate portion 6c of the conductor 6 extends between and contacts at least two neighboring convolutions of the conductor 3. A first portion 6b of the conductor 6 is adjacent to the internal surface of the electrode 5 and is connected thereto by a solder or weld joint 13.

The lead 1 of the '643 patent allows for positive connections between all of components in electrical contact. All connections are internal to the lead, thereby shielding the connections from the body's environment. Both of these factors contribute to the lead's increased reliability. However, the necessity for the third conductor 6 to make the connection between the second conductor 3 and the second electrode 5 increases the difficulty of assembly. Also, the use of coiled wires of different radius 3,4 increases the size of the lead and the fabrication process complexity.

Therefore, there is a need in the art for an elongated electrical lead capable of providing multiple, independent electrical connections while maintaining a small size and a simple assembly process relative to the prior art. Further, it is desired that the lead's internal electrical connections be substantial and be protected from the ambient environment in order to allow reliable operation.

SUMMARY OF THE INVENTION

The subject invention is directed to a new and useful electrical lead, and more particularly, to a new electrode assembly as part of an electrical lead and a method for making the same. The disclosed lead and electrode assembly allow for multiple, independent electrical connections to be provided by a lead of relatively small size as compared to the relevant art. Also, such a lead and electrode assembly incorporate substantial bonds between all of the electrically connected parts, and provide a means for protecting the connections from the abmient environment, thereby increasing the mechanical reliability. Finally, the assembly process for the lead and electrode assembly is relatively simple when compared to the relevant art.

One aspect of the subject invention is an electrode assembly for an elongated implantable lead containing at least one conductor. The electrode assembly has a first support hull for partially surrounding a portion of the lead. The electrode assembly also has an electrode hull for partially surrounding the support hull and a portion of the lead adjacent to the support hull. The electrode hull is securable to the support hull and to the lead at a location axially spaced from the support hull, such that the electrode hull, the support hull, and the lead define a gap. The gap allows the conductor to extend thereinto to operatively connect to the first support hull. In a preferred embodiment, the electrode assembly also has a second support hull for partially surrounding the lead at a location proximal to, but axially spaced from, the first support hull. This second support hull is partially surroundable by, and securable to, the electrode hull, and further defines the gap.

Another aspect of the invention is an implantable lead incorporating an electrode assembly. The lead has an elongated, substantially tubular lead body having opposed proximal and distal end portions and defining a lumen. At least one conductor extends through the lumen of the lead. A connector assembly is located near the proximal end portion of the lead and is capable of interfacing with a first electrical device. The connector assembly is operatively connected to the conductors. An electrode assembly is coupled to the lead body near the distal end portion. The electrode assembly includes a support hull partially surrounding the elongated lead body. Also included in the electrode assembly is an electrode hull partially surrounding both the support hull and a portion of the lead body adjacent to the support hull. The electrode hull is secured to the support hull and to the lead body at a location axially spaced from the support hull, such that a gap is defined by the electrode hull, the support hull, and the lead body. A conductor extends from inside the lead body into the gap to operatively connect to the support hull.

In a preferred embodiment, the electrode assembly incorporates a second support hull. The second support hull partially surrounds the lead body at a location proximal to, but axially spaced from, the first support hull so as to further define the gap. The electrode hull partially surrounds and is secured to the second support hull. A preferred embodiment also includes a second electrical device for interacting with the body. The second electrical device is located near the distal end portion of the lead and is operatively connected to at least one conductor.

Another aspect of the invention is a method for making an implantable electrical lead. The method consists of inserting at least one conductor into a lumen of an elongated lead body, the lead body having opposed proximal and distal end portions. A hole is created in the lead body near the distal end portion. A first support hull is placed around the lead body, with the hole being proximal to the first support hull. At least one conductor is extracted through the hole in the lead body to be connected to the first support hull. An electrode hull is placed around the first support hull and the lead body so that the electrode hull partially surrounds the first support hull and a portion of the lead body adjacent to the support hull. The electrode hull is shaped and placed such that the connection between the conductor and the first support hull is contained in a gap defined by the electrode hull, the first support hull, and the lead body. The electrode hull is secured to the first support hull and also to the lead body at a location axially spaced from the first support hull so that the gap remains between the securing locations. At least one conductor is attached to a connector assembly located near the proximal end portion of the lead.

A preferred method consists of placing a second support hull around the lead body proximal to, but axially spaced from, to the first support hull. As such, the hole in the lead body is located between the first and second support hulls. The electrode hull is secured to and partially surrounds the second support hull. A preferred method also consists of attaching an electrical device to the lead body near the distal end portion, and attaching at least one conductor to the electrical device. A preferred method further consists of winding at least one conductor to form a coil.

It should be appreciated that the present invention can be implemented and utilized in numerous ways. These and other unique features of the system disclosed herein will become more readily apparent from the following description and the accompanying drawings.

BRIEF DESCRIPTION OF THE DRAWINGS

So that those having ordinary skill in the art to which the disclosed invention appertains will more readily understand how to make and use the same, reference may be had to the drawings wherein:

FIG. 1 is a side elevational view of a bipolar pacing lead configured for active fixation, the lead having opposed proximal and distal end portions and including an electrode assembly near the distal end of the lead, the lead and electrode assembly together constituting one aspect of the subject invention;

FIG. 2 is an enlarged localized view of an electrode assembly for an implantable electrical lead, the electrode assembly in accordance with a preferred embodiment of the subject invention; and FIG. 3 is a cross-sectional view taken along line 3—3 of FIG. 2, illustrating the internal wiring configuration of an electrode assembly, in accordance with a preferred embodiment of the subject invention.

FIG. 4 is a cross-sectional view taken along line 4—4 of FIG. 2, illustrating the lead conducting filars arranged in a coil, the lead body, a support hull, and an anode hull, in accordance with a preferred embodiment of the subject invention.

FIG. 5 is a cross-sectional view taken along line 5—5 of FIG. 2, illustrating the lead conducting filars arranged in a coil, the lead body, an anode hull, and a gap between the anode hull and the lead body in which the connections between the lead conductors and assembly are contained, in accordance with a preferred embodiment of the subject invention.

DETAILED DESCRIPTION OF PREFERRED EMBODIMENTS

Figure 6:
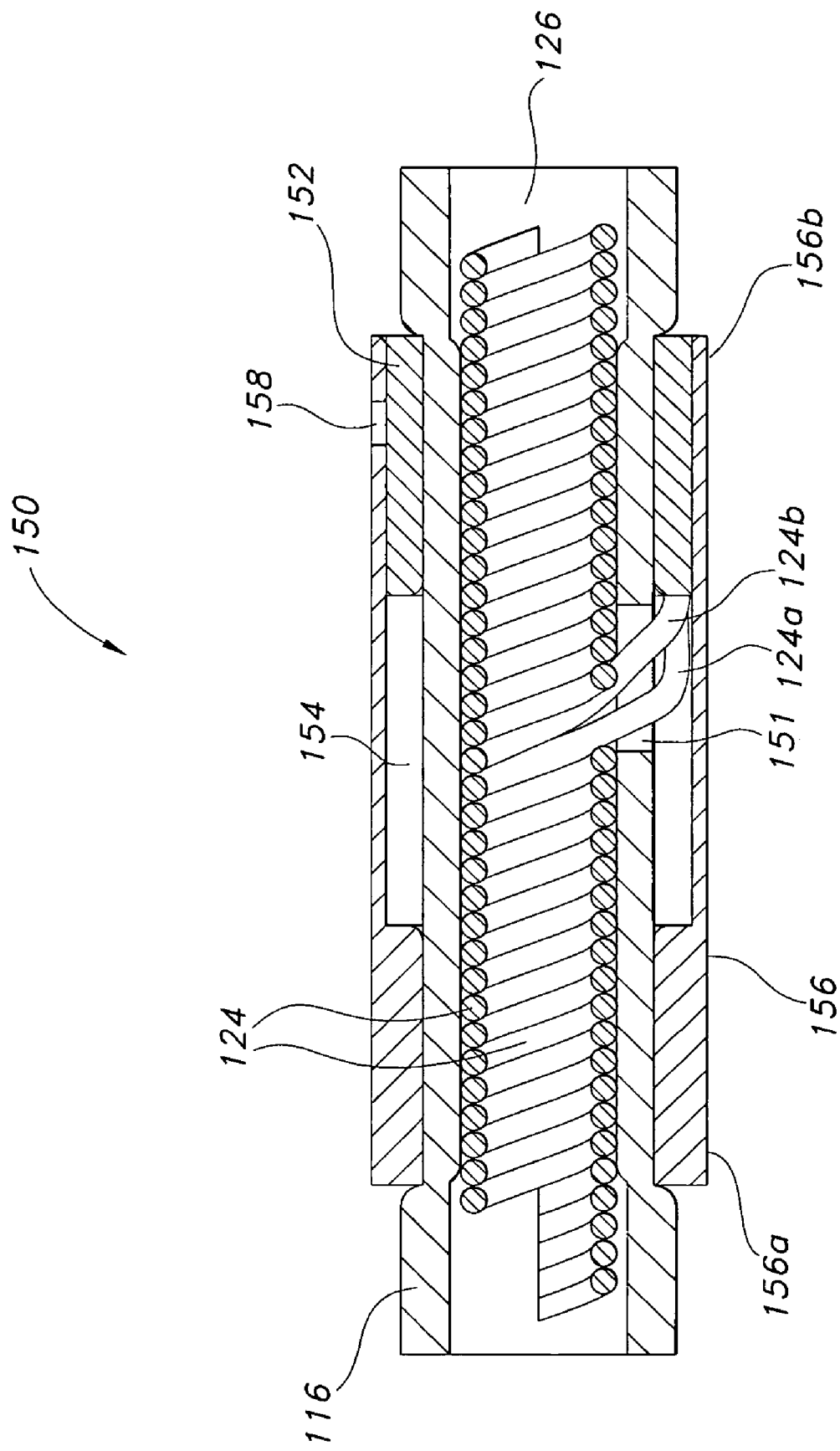
FIG. 6 is a cross-sectional view of an electrode assembly in which only one support hull is utilized, the anode hull being shaped to create a gap within the electrode assembly.

The present invention overcomes many of the prior art problems associated with implantable electrical leads. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Referring now to FIG. 1, there is illustrated a lead 10 for bipolar endocardial pacing and configured for active fixation in the heart. In the description that follows, the term "distal" shall refer, for any object, to an end portion that is farthest from the external electrical device to which the lead connects, and the term "proximal" shall refer, for any object, to the end portion that is nearest to the external electrical device to which the lead connects.

Referring to FIG. 1, the lead 10 has an elongated, tubular lead body 16 which defines a lumen 26. A cathodic electrode 18 is located near the distal end portion 12 of the lead 10. An anodic electrode assembly 50 is proximal to the cathodic electrode 18, such that the two together are capable of providing an electrical impulse to the heart. A helical fixation screw 20 at the distal end of the lead 10 facilitates active fixation to the heart. Other embodiments could have the positions of the cathodic electrode 18 and anodic electrode assembly 50 reversed, or could include a means for passive fixation of the lead to the heart, as would be appreciated by those of ordinary skill in the art. A connector assembly 22 is attached near the proximal end portion 14 of the lead 10 for connecting the lead 10 to an external electrical device. The lead 10 might connect to, without limitation, a pulse generator, pacemaker, or defibrillator. In a preferred embodiment, the connector assembly 22 is a conventional IS-1 type connector. In another embodiment, the lead 10 and electrical device are integrated into a single component.

FIG. 2 shows a magnified view of the lead 10 in the area of the anodic electrode assembly 50. FIG. 3 shows a cross-sectional view of the electrode assembly 50 of FIG. 2. Referring to FIG. 3, multiple conducting filars 24 extend through the lumen 26. The filars 24 are arranged in a coil and are connected to the connector assembly 22 at the proximal end 14 of the lead 10. It is envisioned that one or more of the filars 24 extend to the distal end portion 12 of the lead 10 to connect to the cathodic electrode 18, while other filars 24 connect to the anodic electrode assembly 50. The electrode assembly 50 and connection of the filars 24 thereto is described in greater detail below with respect to FIGS. 3–5. It is preferred that the lead contain six filars, with one pair connected to the cathodic electrode 18 and another pair 24a,24b connected to the anodic electrode assembly 50. In another embodiment, the filars 24 may be straight or otherwise configured.

Referring now to FIGS. 4 and 5 as well as FIG. 3, the anodic electrode assembly 50 includes first 52a and second 52b tubular conducting support hulls. The support hulls 52a,52b surround, and are concentric with, the lead body 16, and are axially spaced with respect to one another so as to form a gap 54 therebetween. A tubular, conducting electrode hull 56 surrounds and is secured to the first and second support hulls 52a,52b. In another embodiment, the support hulls 52a,52b and the electrode hull 56 only partially surround the lead body 16.

As best shown in FIG. 3, two of the filars 24a,24b extend from inside the lead body 16 into the gap 54 to operatively connect to the second support hull 52b. In another embodiment, the filars 24a,24b connect to the first support hull 52a. In still another embodiment, the filars 24a,24b connect both support hulls 52a,52b.

Still referring to FIG. 3, a preferred method for assembling the lead 10 involves inserting several conducting filars 24 into the lumen 26 of the lead body 16, the lead body 16 having opposed proximal 14 and distal 12 end portions. The filars 24 are coiled prior to insertion. All of the filars 24 are attached at one of their ends to a connector assembly 22 secured near the proximal end portion 14 of the lead 10. Some of the filars 24, preferably two, are attached to an electrode 18 located near the distal end portion 12 of the lead 10. Several more (preferably two more) of the filars 24 are attached to an electrode assembly 50 located proximal to the electrode 18. The method for creating the electrode assembly 50 and the connection of the filars 24 thereto is described in more detail in Paragraphs 32–33. In all cases described above, the means for attaching filars 24 to other structures can include soldering, laser welding, and other methods of attachment now known and later developed as would be appreciated by those of ordinary skill in the art.

A hole 51 is created in the lead body 16 near the distal end portion 12. First and second tubular support hulls 52a,52b are placed around the lead body 16 proximal, but not adjacent, to one another, such that the hole 51 in the lead body 16 is located in the gap 54 between the support hulls 52a,52b. In a preferred method, the support hulls 52a,52b are press-fitted around the lead body 16 such that the resulting outer diameter of the support hulls 52a,52b is similar to, or smaller than, that of the lead body 16. Two conductors 24a,24b are extracted through the hole 51 in the lead body 16 and attached to the second support hull 52b. Other methods wherein the filars 24 are attached to the first support hull 52a or to both support hulls 52a, 52b are also envisioned. In one embodiment, illustrated in FIG. 3, the support hull 52b defines a hollow 53 and the filars 24a,24b are attached therein. The attachment can be done by, for example, soldering or laser welding. Preferably, the hole 51 in the lead body 16 is filled with a compatible material, such as a non-conductive adhesive, after extraction of the filars 24.

Two holes 58a,58b are formed radially through a tubular electrode hull 56, the holes 58a,58b being axially spaced from one another. Such holes 58a,58b could be formed, for example, by laser or conventional drilling. The electrode hull 56 is placed around the support hulls 52a,52b so that the electrode hull 56 covers the support hulls 52a,52b and the gap 54 therebetween, and the holes 58a,58b through the electrode hull 56 are directly adjacent to the support hulls 52a,52b. The electrode hull 56 is secured to the support hulls 52a,52b by laser welding the electrode hull 56 to the support hulls 52a,52b through the holes 58a,58b in the electrode hull 56. In another preferred method, the electrode hull 56 is soldered to the support hulls 52a,52b.

In another preferred method, the electrode hull 56 is placed around the support hulls 52a,52b and holes 58a,58b are then formed in the electrode hull 56 to expose the underlying support hulls 52a,52b. Such holes 58a,58b could be formed, for example, by laser or conventional drilling. Still another preferred method involves the first and second support hulls 52a,52b being placed around the lead body 16 followed by the formation of the hole 51 in the lead body 16 through which the filars 24 are later extracted.

In another preferred embodiment, shown in FIG. 6, the anodic electrode assembly 150 contains only one support hull 152. As will be appreciated by those of ordinary skill in the pertinent art, the anodic electrode assembly 150 utilizes the same principles of the anodic electrode assembly 50 described above. Accordingly, like elements are indicated by using reference numerals offset from one another by 100 (e.g. the component designated by reference numeral 116 is substantially the same as the component designated by reference numeral 16). A substantially tubular electrode hull 156 has a uniform outer diameter and portions with smaller 156a and larger 156b inner diameter. The portion with the larger inner diameter 156a surrounds the lead body 116, while the portion with the larger inner diameter 156b surrounds the support hull 152. The electrode hull 156 is positioned such that the thicker section 156*a* is axially spaced from the support hull 152, thus defining a gap 154 therebetween. A pair of filars of the lead 124*a*,124*b* extend from inside the lumen 126 of the lead body 116 into the gap 154 and therein connect to the support hull 152. In another embodiment, the electrode hull has a tapered shape, rather than distinct regions of small and large inner diameter 156*a*,156*b*.

Still referring to FIG. 6, a preferred method to create an electrode assembly 150 utilizing only one support hull 152 is presented. A hole 151 is created in the lead body 116, and a tubular support hull 152 is placed around the lead body 116 proximal to the hole 151. In a preferred method, the support hull 152 is press-fitted around the lead body 116. Two filars 124*a*,124*b* are extracted through the hole 151 in the lead body 116 and attached to the support hull 152. Preferably, the hole 151 in the lead body 116 is filled with a compatible material after extraction of the filars 124*a*,124*b*.

A substantially tubular electrode hull 156, is placed around the support hull 152 and an adjacent portion of the lead body 116 such that the electrode hull 156 covers the hole 151, the extracted filars 124*a*,124*b*, and the connection of the filars 124*a*,124*b* to the support hull 152. In a preferred embodiment, the electrode hull 156 has a uniform outer diameter and portions 156*a*,156*b* of smaller and larger inner diameter, respectively. In such preferred embodiment, the electrode hull 156 is placed such that the portion 156*b* surrounds the support hull 152 and the portion 156*a* surrounds the lead body 116 at a location axially spaced from the support hull 152. The electrode hull 156, the support hull 152, and the lead body 116 thereby define a gap 154 for the filars 124*a*,124*b*. The electrode hull 156 is secured to the support hull 152 by laser welding the electrode hull 156 to the support hull 152 through a hole 158 in the electrode hull 156. In another preferred method, the electrode hull 156 is soldered to the support hull 152. The electrode hull 156 is secured to the lead body 116 by press-fitting the portion 156*a* onto the lead body 116.

FIGS. 1–6 illustrate various embodiments of a novel endocardial pacing lead in which the lead incorporated two electrodes and electrical connections thereto. Other preferred embodiments of the subject invention are envisioned, including leads to be used for epicardial and myocardial applications, for heart applications other than pacing (e.g. defibrillation), and for applications requiring electrical impulses to areas other than the heart. Other preferred embodiments also include leads incorporating only one electrode, or more than two electrodes, or an electrode and a sensor, or other permutations of such structures as would be appreciated by those of ordinary skill in the art.

Although the electrical lead with electrode assembly and method for making the same of the subject invention has been described with respect to preferred embodiments, those skilled in the art will readily appreciate that changes and modifications may be made thereto without departing from the spirit and scope of the present invention as defined by the appended claims.

What is claimed is:

1. An implantable lead comprising:
    a) an elongated lead body having opposed proximal and distal end portions and defining an interior lumen;
    b) electrical conductor extending through the interior lumen of the lead body;
    c) a connector assembly operatively associated with the proximal end portion of the lead body for interfacing with an electrical device, and wherein the connector assembly is operatively connected to the electrical conductor; and
    d) an electrode assembly, operatively associated with the distal end portion of the lead body, the electrode assembly including:
        i) at least one support hull at least partially surrounding an exterior surface portion of the elongated lead body; and
        ii) an electrode hull at least partially surrounding the at least one support hull and an exterior surface portion of the lead body adjacent to the at least one support hull, wherein the electrode hull is directly secured to the support hull, such that a gap is defined by the electrode hull, the support hull and the lead body, and wherein the at electrical conductor extends from the interior lumen of the lead body, through an opening in the lead body and into the gap to operatively connect to the at least one support hull.

2. The lead of claim 1, wherein the conductor is a multifilar conductor, and wherein a first pair of conductive filars is connected to another electrode associated with a distal end of the lead body, and a second pair of conductive filars is connected to the support hull of the electrode assembly.

3. The lead of claim 1, wherein the multifilar conductor is a coiled conductor.

4. The lead of claim 1, wherein the at least one support hull has a hollow for receiving the conductor.

5. The lead of claim 1, wherein the electrode assembly includes a second support hull axially spaced from the at least one support hull to further define the gap, and wherein the electrode hull at least partially surrounds and is secured to the at least one support hull and the second support hull.

6. An implantable lead comprising:
    a) an elongated lead body having opposed proximal and distal end portions and defining an interior lumen;
    b) a connector assembly operatively associated with the proximal end portion of the lead body for connection with an electrical device;
    c) a multifilar conductor extending through the interior lumen of the lead body and operatively connected to the connector assembly;
    d) a cathodic tip electrode operatively associated with the distal end portion of the lead body and operatively connected to the multifilar conductor;
    e) an anodic electrode assembly spaced proximally from the cathodic electrode, the anodic electrode assembly including:
        i) a pair of axially spaced apart support hulls surrounding the elongated lead body; and
        ii) an electrode hull covering the pair of axially spaced apart support hulls to define an annular gap between the lead body and the electrode hull intermediate the axially spaced apart support hulls, wherein filars of the multifilar conductor extend from the interior lumen of the lead body, through an opening in the lead body, and into the annular gap so as to operatively connect to at least one of the axially spaced apart support hulls.

7. An implantable lead as recited in claim 6, wherein at least two filars of the multifilar conductor are operatively connected to at least one of the support hulls of the anodic electrode assembly.

8. An implantable lead as recited in claim 6, wherein filars of the multifilar conductor are operatively connected to both support hulls of the anodic electrode assembly.

9. An implantable lead as recited in claim 6, wherein at least two filars of the multifilar conductor are operatively connected to the cathodic tip electrode.

10. An implantable lead as recited in claim 6, wherein the electrode hull is fixedly secured to the axially spaced apart support hulls.

11. An implantable lead as recited in claim 6, wherein the axially spaced apart support hulls are press-fit onto the lead body.

12. An implantable lead as recited in claim 6, wherein the opening in the lead body is located within the annular gap.

13. An implantable lead as recited in claim 6, wherein the connector assembly is an IS-1 type connector assembly.

14. An implantable lead as recited in claim 6, further comprising a helical fixaton screw at the distal end of the lead body to facilitate active fixation to the heart.

15. An implantable lead comprising:
   a) an elongated lead body having an exterior surface and an interior lumen;
   b) a conductor extending through the interior lumen of the lead body;
   c) an electrode assembly including a pair of axially spaced apart support hulls surrounding portions of the exterior surface of the lead body and an electrode hull covering the pair of axially spaced apart support hulls to define an annular gap between the lead body and the electrode hull intermediate the axially spaced apart support hulls, wherein the conductor extends from the interior lumen of the lead body, through an opening in the lead body, and into the annular gap for connection with at least one of the axially spaced apart support hulls.

16. An implantable lead as recited in claim 15, wherein the conductor is a multifilar conductor and at least two conductive filars thereof are operatively connected to at least one of the axially spaced apart support hulls of the electrode assembly.

17. An implantable lead as recited in claim 15, wherein the electrode hull is fixedly secured to the axially spaced apart support hulls.

18. An implantable lead as recited in claim 15, wherein the axially spaced apart support hulls are press-fit onto the lead body.

* * * * *

UNITED STATES PATENT AND TRADEMARK OFFICE
CERTIFICATE OF CORRECTION

| | |
|---|---|
| PATENT NO. | : 7,197,361 B2 |
| APPLICATION NO. | : 10/911975 |
| DATED | : March 27, 2007 |
| INVENTOR(S) | : Ronald A. van den Nieuwenhof et al. |

It is certified that error appears in the above-identified patent and that said Letters Patent is hereby corrected as shown below:

Claim 1, Col. 8, line 16, delete the word "at"

Signed and Sealed this

Nineteenth Day of June, 2007

JON W. DUDAS
*Director of the United States Patent and Trademark Office*